United States Patent
Zhao

(10) Patent No.: US 9,695,376 B2
(45) Date of Patent: Jul. 4, 2017

(54) DIALKYL CARBONATES, METHODS FOR THEIR PRODUCTION AND USE

(71) Applicant: Huntsman Petrochemical LLC, The Woodlands, TX (US)

(72) Inventor: Haibo Zhao, The Woodlands, TX (US)

(73) Assignee: Huntsman Petrochemical LLC, The Woodlands, TX (US)

(*) Notice: Subject to any disclaimer, the term of this patent is extended or adjusted under 35 U.S.C. 154(b) by 0 days.

(21) Appl. No.: 15/116,286

(22) PCT Filed: Feb. 13, 2015

(86) PCT No.: PCT/US2015/015736
§ 371 (c)(1),
(2) Date: Aug. 3, 2016

(87) PCT Pub. No.: WO2015/123486
PCT Pub. Date: Aug. 20, 2015

(65) Prior Publication Data
US 2017/0009173 A1    Jan. 12, 2017

Related U.S. Application Data

(60) Provisional application No. 61/939,533, filed on Feb. 13, 2014.

(51) Int. Cl.
| | |
|---|---|
| *C07C 69/96* | (2006.01) |
| *C10M 105/48* | (2006.01) |
| *C10M 129/84* | (2006.01) |
| *C07C 68/06* | (2006.01) |

(52) U.S. Cl.
CPC ............ *C10M 129/84* (2013.01); *C07C 68/06* (2013.01); *C07C 69/96* (2013.01); *C10M 105/48* (2013.01); *C10M 2207/32* (2013.01); *C10M 2207/325* (2013.01); *C10N 2230/02* (2013.01); *C10N 2230/06* (2013.01); *C10N 2240/04* (2013.01); *C10N 2240/08* (2013.01); *C10N 2240/102* (2013.01); *C10N 2240/30* (2013.01); *C10N 2270/00* (2013.01)

(58) Field of Classification Search
CPC .......................... C10M 2207/32; C07C 68/005
USPC .......................................... 508/462; 558/277
See application file for complete search history.

(56) References Cited

U.S. PATENT DOCUMENTS

| | | |
|---|---|---|
| 2,758,975 A | 8/1956 | Cottle et al. |
| 5,206,408 A | 4/1993 | Liotta, Jr. |
| 5,290,464 A | 3/1994 | Fisicaro et al. |
| 5,387,374 A | 2/1995 | Westfechtel et al. |
| 5,986,125 A | 11/1999 | Reuter et al. |
| 8,338,631 B2 | 12/2012 | Risse et al. |
| 8,629,295 B2 | 1/2014 | Koh et al. |
| 2004/0242914 A1 | 12/2004 | Ridinger et al. |
| 2006/0263604 A1 | 11/2006 | Martin et al. |
| 2011/0250160 A1 | 10/2011 | Banowski et al. |

*Primary Examiner* — Vishal Vasisth
(74) *Attorney, Agent, or Firm* — Huntsman International LLC

(57) ABSTRACT

The present disclosure provides a dialkyl carbonate prepared from a methyl branched primary $C_{16}$-$C_{17}$ alcohol. The dialkyl carbonate is prepared by transesterifying a reactant dialkyl carbonate with the methyl branched primary $C_{16}$-$C_{17}$ alcohol under transesterification reaction conditions. The subsequently produced dialkyl carbonate may be used in various applications, including, but not limited to, in lubricating, cosmetic and textile products and applications.

14 Claims, No Drawings

DIALKYL CARBONATES, METHODS FOR THEIR PRODUCTION AND USE

CROSS-REFERENCE TO RELATED APPLICATIONS

This application is the National Phase of International Application PCT/US2015/015736 filed Feb. 13, 2015 which designated the U.S. and which claims priority to U.S. App. Ser. No. 61/939,533 filed Feb. 13, 2014. The noted applications are incorporated herein by reference.

FIELD OF THE INVENTION

The present disclosure is directed to dialkyl carbonates, methods for their production and their use in various applications, for example, in lubricating compositions.

BACKGROUND INFORMATION

Because of their physical and chemical properties and performance characteristics, dialkyl carbonates have been used in various applications, such as in lubricant base fluids and as performance fluid components. Several methods for producing dialkyl carbonates have been generally described by Leslie Rudnick in "Synthetics, Mineral Oils, and Bio-Based Lubricants: Chemistry and Technology, Second Edition" including their production from: alkyl halides; carboalkoxides; phosgene; carbon dioxide; and syntheses by transesterification. Various improvements to such general methods can be found in: U.S. Pat. No. 2,758,975 which describes the use of phosgene and alcohols; U.S. Pat. Nos. 5,290,464 and 5,387,374 which disclose transesterification processes of certain essentially linear aliphatic al alcohols or Guerbet alcohols and lower dialkyl carbonates; U.S. Pat. No. 5,986,125 which teaches a process for preparing symmetrical dialkyl carbonates by carrying out transesterification in reaction columns that allow the reactants to flow countercurrent to one another; US Pat. Publ. No. 2004/0242914 which discloses a process for producing low odor dialkyl carbonates using two rectification steps and one deodorization step; U.S. Pat. No. 8,338,631 which describes a continuous process for preparing dialkyl carbonates in a reaction column by introducing a cyclic alkylene carbonate and lower alcohol into different parts of the column and allowing them to flow countercurrent to one another; and U.S. Pat. No. 8,629,295 which teaches a process for preparing dialkyl carbonate from urea, an alkyl alcohol and an ionic liquid containing a cation.

SUMMARY OF THE INVENTION

The present disclosure relates to a dialkyl carbonate of a methyl branched primary $C_{16}$-$C_{17}$ alcohol having a structure according to formula (I):

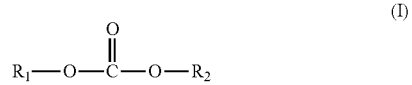

(I)

where $R_1$ is a methyl branched $C_{16}$-$C_{17}$ alkyl group; and $R_2$ has the same meaning as $R_1$ or is an alkyl group having 1 to 20 carbon atoms, an alicyclic group having 3 to 20 carbon atoms or an aralkyl group having 6 to 20 carbon atoms.

In a further embodiment, the present disclosure provides a process for preparing the dialkyl carbonate of formula (I) by transesterifying a reactant dialkyl carbonate with a methyl branched $C_{16}$-$C_{17}$ alcohol.

Because of its physical and chemical properties, the dialkyl carbonate of formula (I) may be used in various applications and products, including, but not limited to, lubricating, cosmetic and textile applications and products.

DETAILED DESCRIPTION

If appearing herein, the term "comprising" and derivatives thereof are not intended to exclude the presence of any additional component, step or procedure, whether or not the same is disclosed herein. In order to avoid any doubt, all formulations claimed herein through use of the term "comprising" may include any additional additive, adjuvant, or compound, unless stated to the contrary. In contrast, the term, "consisting essentially of" if appearing herein, excludes from the scope of any succeeding recitation any other component, step or procedure, excepting those that are not essential to operability and the term "consisting of", if used, excludes any component, step or procedure not specifically delineated or listed. The term "or", unless stated otherwise, refers to the listed members individually as well as in any combination.

The articles "a" and "an" are used herein to refer to one or to more than one (i.e. to at least one) of the grammatical object of the article. By way of example, "a free radical scavenger" means one free radical scavenger or more than one free radical scavenger.

The phrases "in one embodiment," "according to one embodiment," and the like generally mean the particular feature, structure, or characteristic following the phrase is included in at least one embodiment of the present invention, and may be included in more than one embodiment of the present invention. Importantly, such phrases do not necessarily refer to the same embodiment.

If the specification states a component or feature "may", "can", "could", or "might" be included or have a characteristic, that particular component or feature is not required to be included or have the characteristic.

The present disclosure provides dialkyl carbonates of branched monomethyl $C_{16}$-$C_{17}$ alcohols having unique properties which make them suitable for use in various applications and products including, but not limited to, in lubrication, cosmetic and textile applications and products. The dialkyl carbonates of the present disclosure surprisingly exhibit high lubricity, high biodegradability, excellent anti-wear, low pour point, high kinematic viscosity, are resistant to hydrolysis and oxidation, and are highly compatible with mineral oils and synthetic fluids.

Thus, in one aspect, the present disclosure provides a dialkyl carbonate of a methyl branched primary $C_{16}$-$C_{17}$ alcohol having a structure according to formula (I):

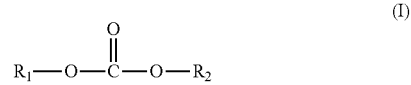

(I)

where $R_1$ is a methyl branched $C_{16}$-$C_{17}$ alkyl group; and $R_2$ has the same meaning as $R_1$ or is an alkyl group having 1 to 20 carbon atoms, an alicyclic group having 3 to 20 carbon atoms or an aralkyl group having 6 to 20 carbon atoms. In a further embodiment, $R_2$ has the same meaning as $R_1$ or is an alkyl group having 1 to 10 carbon atoms, an alicyclic group having 3 to 10 carbon atoms or an aralkyl group having 6 to 10 carbon atoms According to one embodiment, $R_1$ and $R_2$ are methyl branched $C_{16}$-$C_{17}$ alkyl groups. In another embodiment, $R_1$ is a methyl branched $C_{16}$-$C_{17}$ alkyl group and $R_2$ is an alkyl group having 1-10 carbon atoms. In still another embodiment, $R_1$ is a methyl branched $C_{16}$-$C_{17}$ alkyl group and $R_2$ is an alkyl group having 1 to 4 carbon atoms. In yet another embodiment, $R_1$ is a methyl branched $C_{16}$-$C_{17}$ alkyl group and $R_2$ is a methyl or ethyl group.

In a further embodiment, $R_1$ is a methyl branched $C_{16}$-$C_{17}$ alkyl group and $R_2$ is an aralkyl group having 6 to 20 carbon atoms, or in some embodiments 6 to 10 carbon atoms. In still another embodiment, $R_1$ is a methyl branched $C_{16}$-$C_{17}$ alkyl group and R2 is a benzyl group.

In another aspect, the present disclosure provides a process for producing the dialkyl carbonate of formula (I) by transesterifying a reactant dialkyl carbonate with a methyl branched $C_{16}$-$C_{17}$ alcohol.

According to one embodiment, the reactant dialkyl carbonate is a compound having a structure according to formula (II):

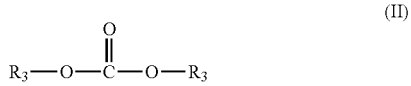

(II)

where $R_3$ is an alkyl group having 1 to 20 carbon atoms, an alicyclic group having 3 to 20 carbon atoms or an aralkyl group having 6 to 20 carbon atoms. In a further embodiment, $R_3$ is an alkyl group having 1 to 10 carbon atoms, an alicyclic group having 3 to 10 carbon atoms or an aralkyl group having 6 to 10 carbon atoms. Examples of $R_3$ as an alkyl group include methyl, ethyl, propyl, allyl, butyl, butenyl, pentyl, hexyl, heptyl, octyl, nonyl and decyl. Examples of $R_3$ as an alicyclic group include cyclopropyl, cyclohexyl, cyclohexylmethyl and cycloheptyl. Examples of $R_3$ as an aralkyl group include benzyl, phenethyl, phenylpropyl, phenylbutyl and methylbenzyl.

In some embodiments, the above-mentioned alkyl group, alicyclic group and aralkyl group may be substituted with a substituent, such as a $C_1$-$C_3$ alkyl group, a $C_1$-$C_3$ alkoxy group, a cyano group and a halogen, as long as the number of carbon atoms of the substituted group does not exceed 20, and it may also contain an unsaturated bond.

According to one embodiment, $R_3$ is selected from dimethyl carbonate, diethyl carbonate, dipropyl carbonate, diallyl carbonate, dibutenyl carbonate, dibutyl carbonate, dipentyl carbonate, dihexyl carbonate, diheptyl carbonate, dioctyl carbonate, dinonyl carbonate, didecyl carbonate, dicyclopentyl carbonate, dicyclohexyl carbonate, dicycloheptyl carbonate, dibenzyl carbonate, diphenethyl carbonate, di(phenylpropyl) carbonate, di(phenylbutyl) carbonate, di(chlorobenzyl) carbonate, di(methoxybenzyl) carbonate, di(methoxymethyl) carbonate, di(methoxyethyl) carbonate, di(chloroethyl) carbonate, di(cyanoethyl) carbonate and a mixture thereof.

In another particular embodiment, $R_3$ is a lower alkyl group having 1 to 4 carbon atoms. In still another embodiment, $R_3$ is methyl.

The methyl branched primary $C_{16}$-$C_{17}$ alcohol used in transesterifying the reactant dialkyl carbonate is generally a mixture comprising alcohols with different, consecutive carbon numbers. According to one embodiment, the methyl branched primary $C_{16}$-$C_{17}$ alcohol comprises alcohols having a carbon number in the range of from 11 to 22, of which alcohols, at least a portion of the alcohols are methyl branched and optionally ethyl branched. Typically at least 75% by weight, more typically at least 90% by weight of the total weight of such mixture of alcohols represent a range of alcohols in which the heaviest alcohol comprises at most 6 carbon atoms more than the lightest alcohol. Thus, in another embodiment, the methyl branched primary $C_{16}$-$C_{17}$ alcohol comprises at least 75% by weight alcohols having a carbon number in the range of from 14 to 20, of which alcohols, at least a portion of the alcohols are methyl branched and where the % by weight is based on the total weight of the methyl branched primary $C_{16}$-$C_{17}$ alcohol. In still further embodiments, the methyl branched primary $C_{16}$-$C_{17}$ alcohol comprises at least 99.99% by weight alcohols having a carbon number in the range of from 14 to 20, of which alcohols, at least a portion of the alcohols are methyl branched and where the % by weight is based on the total weight of the methyl branched primary $C_{16}$-$C_{17}$ alcohol.

In still other embodiments, at least 75% by weight, and in other embodiments at least 80% by weight, based on the total weight of the methyl branched primary $C_{16}$-$C_{17}$ alcohol, contains alcohols having a carbon number in the range of from 16 to 17, of which alcohols, at least a portion of the alcohols are methyl branched and optionally ethyl branched.

In another embodiment, the average number of branches per alcohol present in the methyl branched primary $C_{16}$-$C_{17}$ alcohol is at least 0.8. In a further embodiment, the average number of branches per alcohol present in the methyl branched primary $C_{16}$-$C_{17}$ alcohol is at least 0.9. In yet other embodiments, the average number of branches per alcohol present in the methyl branched primary $C_{16}$-$C_{17}$ alcohol is about 1.0. In still other embodiments, the average number of branches per alcohol present in the methyl branched primary $C_{16}$-$C_{17}$ alcohol is at most 2.0.

In another embodiment, the average number of branches per alcohol present in the methyl branched primary $C_{16}$-$C_{17}$ alcohol is at most 1.5.

According to one embodiment, the number of methyl branches in the methyl branched primary $C_{16}$-$C_{17}$ alcohol is at least 20% of the total number of branches. In another embodiment, the number of methyl branches in the methyl branched primary $C_{16}$-$C_{17}$ alcohol is at least 40% of the total number of branches. In still another embodiment, the number of methyl branches in the methyl branched primary $C_{16}$-$C_{17}$ alcohol is at least 50% of the total number of branches. In yet another embodiment, the number of methyl branches in the methyl branched primary $C_{16}$-$C_{17}$ alcohol is at least 90% of the total number of branches. In a further embodiment, the number of methyl branches in the methyl branched primary $C_{16}$-$C_{17}$ alcohol is at most 99.9%, more typically at most 98% of the total number of branches. If present, the number of ethyl branches in the methyl branched primary $C_{16}$-$C_{17}$ alcohol may be at least 0.1%, more generally at least 1%, and may be even at least 2% of the total number of branches. In other embodiments, the number of ethyl branches in the methyl branched primary $C_{16}$-$C_{17}$ alcohol may be at most 20%, more frequently at most 10% of the total number of branches. The number of any branches, if present, other than methyl or ethyl in the methyl branched primary $C_{16}$-$C_{17}$ alcohol may be less than 10%, and in particular, may be less than 5% of the total number of branches.

In a different embodiment, the content of branched primary alcohols in the methyl branched primary $C_{16}$-$C_{17}$ alcohol is at least 70% by weight, more typically at least 90% by weight, based on the total weight of the methyl branched primary $C_{16}$-$C_{17}$ alcohol. In other embodiments, the content of branched primary alcohols in the methyl branched primary $C_{16}$-$C_{17}$ alcohol is at least 95% by weight, more typically at least 99.99% by weight, based on the total weight of the methyl branched primary $C_{16}$-$C_{17}$ alcohol. In some embodiments, the content of linear alcohols in the methyl branched primary $C_{16}$-$C_{17}$ alcohol is typically at most 30% by weight, more typically at most 10% by weight, based on the total weight of the methyl branched primary $C_{16}$-$C_{17}$ alcohol. In different embodiments, the content of linear alcohols in the branched primary $C_{16}$-$C_{17}$ alcohol is at most 5% by weight, more typically at most 0.01% by weight, based on the total weight of the methyl branched primary $C_{16}$-$C_{17}$ alcohol.

According to one particular embodiment, the methyl branched primary $C_{16}$-$C_{17}$ alcohol may be a monomethyl branched primary $C_{16}$-$C_{17}$ alcohol represented by the following formula:

$$CH_3-CH_2-CH_2-CH_2-CH_2-CH_2-CH_2-\underset{\underset{CH_3}{|}}{CH_2}-CH_2-CH_2-CH_2-CH_2-CH_2-CH_2-CH_2-OH$$

$$CH_3-CH_2-CH_2-CH_2-CH_2-CH_2-CH_2-CH_2-\underset{\underset{CH_3}{|}}{CH_2}-CH_2-CH_2-CH_2-CH_2-CH_2-CH_2-CH_2-OH$$

In the above formula, branching in the monomethyl branched $C_{16}$-$C_{17}$ alcohol may vary from the second carbon to the fourteenth or fifteenth carbon in the linear chain.

The methyl branched primary $C_{16}$-$C_{17}$ alcohol may be prepared by means known to one skilled in the art. For example, the methyl branched primary $C_{16}$-$C_{17}$ alcohol may be prepared from branched olefins by hydroformylation, by oxidation and hydrolysis, by sulphation and hydration, by epoxidation and hydration, or the like. In one particular embodiment, the methyl branched primary $C_{16}$-$C_{17}$ alcohol may be prepared as described in EP 1767512, the contents of which is incorporated herein by reference, wherein the branched olefins are converted into methyl branched primary $C_{16}$-$C_{17}$ alcohols by reaction with carbon monoxide and hydrogen in the presence of a hydroformylation catalyst and optional inert solvent.

A commercially available methyl branched primary $C_{16}$-$C_{17}$ alcohol is sold under the trade name Neodol® 67 primary alcohol (Shell Chemical Co.). The typical chain distribution for the Neodol® 67 alcohol is as follows:

| Property | Unit | Value |
|---|---|---|
| $C_{14}$ and lower alcohols | % w/w | <0.5 |
| $C_{15}$ alcohol | % w/w | 5 |
| $C_{16}$ alcohol | % w/w | 31 |
| $C_{17}$ alcohol | % w/w | 54 |
| $C_{18}$ alcohol | % w/w | 7 |
| $C_{19}$ alcohol | % w/w | 2 |
| $C_{20}$ and higher alcohols | % w/w | <0.2 |
| Total hydrocarbons, max | % w/w | 0.5 |

In another embodiment, the methyl branched primary $C_{16}$-$C_{17}$ alcohol may be combined with one or more other alcohols known in the art for transesterifying a dialkyl carbonate. Examples include fatty alcohols such as caproic alcohol, caprylic alcohol, 2-ethylhexyl alcohol, capric alcohol, 2-butyl-1-octanol, lauryl alcohol, isotridecyl alcohol, myristyl alcohol, cetyl alcohol, 2-hexyl-1-decanol, palmitoleyl alcohol, stearyl alcohol, isostearyl alcohol, oleyl alcohol, elaidyl alcohol, petroselinyl alcohol, linolyl alcohol, linolenyl alcohol, 2-octyl-1-dodecanol, elaeostearyl alcohol, arachyl alcohol, gadoleyl alcohol, behenyl alcohol, erucyl alcohol and brassidyl alcohol and the technical mixtures thereof obtained, for example, in the high-pressure or low-pressure hydrogenation of technical methyl esters based on fats and oils or aldehydes from Roelen's oxosynthesis and as monomer fraction in the dimerization of unsaturated fatty alcohols. Other alcohols include Guerbet alcohols having 22 to 44 carbon atoms, alkoxylated alcohols, preferably of the alcohols mentioned above containing 1 to 20 and preferably 2 to 10 ethylene and/or propylene oxide units per molecule, aromatic alcohols, such as benzyl alcohol, cycloaliphatic alcohols, such as cyclohexanol, methanol, ethanol, isopropanol, t-butyl alcohol, t-amyl alcohol and n-octyl alcohol.

According to one embodiment, the transesterification is carried out in the presence of a transesterification catalyst. The transesterification catalyst may be for example a hydride, oxide, hydroxide, alkoxide, amide or salt of an alkali metal such as lithium, sodium, potassium, rubidium and cesium, preferably of sodium and potassium. Salts of alkali metals can be those of organic or inorganic acids, for example, of acetic acid, propionic acid, butyric acid, benzoic acid, stearic acid, carbonic acid (carbonates or hydrogen carbonates), of hydrochloric acid, hydrobromic acid or hydroiodic acid, nitric acid, sulphuric acid, hydrofluoric acid, phosphoric acid, hydrocyanic acid, thiocyanic acid, boric acid, stannic acid, $C_1$-$C_4$ stannonic acids or antimonic acids. As compounds of alkali metals, preference is given to the oxides, hydroxides, alkoxides, acetates, propionates, benzoates, carbonates and hydrogen carbonates, with particular preference being given to using hydroxides, alkoxides, acetates, benzoates or carbonates. According to one embodiment, such alkali metal compounds are used in amounts of from 0.001 to 2% by weight, in other embodiments from 0.003 to 1.0% by weight, and in even other embodiments from 0.005 to 1.0% by weight, based on the total weight of the transesterification reaction mixture.

According to another embodiment, it is possible, if appropriate, to add complexing substances to the alkali metal compounds. Examples which may be mentioned are crown ethers such as dibenzo-18-crown-6, polyethylene glycols or bicyclic nitrogen-containing cryptands. Such complexing agents may be used in amounts of from 0.1 to 200 mol %, or from 1 to 100 mol %, based on the alkali metal compound.

Further examples of transesterification catalysts for the process of this disclosure are thallium(I) and thallium(III) compounds such as the oxides, hydroxides, carbonates, acetates, bromides, chlorides, fluorides, formates, nitrates, cyanates, stearates, naphthenates, benzoates, cyclohexylphosphonates, hexahydrobenzoates, cyclopentandienylthallium, thallium methoxide, thallium ethoxide, preferably Tl(I) oxide, Tl(I) hydroxide, Tl(I) carbonate, Tl(I) acetate, Tl(III) acetate, Tl(I) fluoride, Tl(I) formate, Tl(I) nitrate, Tl(I) naphthenate and Tl—(I) methoxide. The amounts of thallium catalyst are not particularly critical. They are generally 0.0001-10% by weight, or in further embodiments 0.001-1% by weight, based on the total weight of the transesterification reaction mixture.

Nitrogen-containing bases can also be used as transesterification catalysts in the process of this disclosure. Mention may be made by way of example of secondary or tertiary amines such as triethylamine, tributylamine, methyldibenzylamine, dimethylcyclohexylamine, etc. The amounts used according to the present disclosure of the nitrogen-containing bases may be from 0.01 to 10% by weight, or from 0.1 to 5% by weight, or even further from 0.1 to 1% by weight, based on the total weight of the transesterification reaction mixture.

According to the present disclosure, compounds from the group consisting of phosphines, stibines, arsines and divalent sulphur and selenium compounds and also their onium salts may also be used as transesterification catalysts. Mention may be made by way of example of the following: tributylphosphine, triphenylphosphine, diphenylphosphine, 1,3-bis(diphenylphosphino)propane, triphenylarsine, trimethylarsine, tributylamine, 1,2-bis(diphenylarsino)ethane, triphenylantimony, diphenyl sulphide, diphenyl disulphide, diphenyl selenide, tetraphenylphosphonium halide (Cl, Br, I), tetraphenylarsonium halide (Cl, Br, I), triphenylsulphonium halide (Cl, Br), etc. The amounts used according to this disclosure in the case of this group of transesterification catalysts may be in the range from 0.1 to 10% by weight, or from 0.1 to 5% by weight, or even further from 0.1 to 2% by weight, based on the total weight of the transesterification reaction mixture.

Furthermore, complexes or salts of tin, titanium or zirconium may also be used as a transesterification catalyst according to the present disclosure. Examples of such complexes or salts are butylstannonic acid, tin methoxide, dimethyltin, dibutyltin oxide, dibutyltin dilaurate, tributyltin hydride, tributyltin chloride, tin(II) ethylhexanoate, zirconium alkoxides (methyl, ethyl, butyl), zirconium(IV) halides (F, Cl, Br, I), zirconium nitrates, zirconium acetylacetonate, titanium alkoxides (methyl, ethyl, isopropyl), titanium acetate, titanium acetylacetonate, etc. The amounts which may be used are from 0.1 to 10% by weight, or from 0.1 to 5% by weight, based on the total weight of the transesterification reaction mixture.

It is also possible to use bifunctional transesterification catalysts of the formula $[A_a X_b]_m [B_c Y_d]_n$ in the process of the present disclosure. In these bifunctional transesterification catalysts, the molar ratio of the two components in square brackets is expressed by the indices m and n. These indices can, independently of one another, assume values of 0.001-1, preferably 0.01-1, particularly preferably 0.05-1 and very particularly preferably 0.1-1. Within the square brackets are uncharged salts in each case composed of a cation and an anion. The indices a and b are, independently of one another, integers of 1-5; the indices c and d are, independently of one another, integers of 1-3, matching the requirements of the valencies of the cations and anions to form such uncharged salts. Furthermore, A is the cation of a metal belonging to the third period and group IIa, the fourth period and group IIa, IVa-VIIIa, Ib or IIb, the fifth period and group IIa, IVa-VIIa or IVb or the sixth period and group IIa-VIa of the Periodic Table of the Elements in the short period form. Possible metals for the cation A are taken by a person skilled in the art from the usual depictions of the Periodic Table of the Elements in the short period form. A is preferably the cation of one of the metals Mg, Ca, Sr, Ba, Zn, Cu, Mn, Co, Ni, Fe, Cr, Mo, W, Ti, Zr, Sn, Hf, V and Ta, preferably the cation of one of the metals Mg, Ca, Zn, Co, Ni, Mn, Cu and Sn. Apart from the uncomplexed cations of the metals mentioned, cationic oxo complexes of the metals mentioned are also possible, for example titanyl TiO.sup.++ and chromyl CrO.sub.2.sup.++. The anion X associated with the cation A is that of an inorganic or organic acid. Such an inorganic or organic acid can be monobasic or dibasic or tribasic. Such acids and their anions are known to those skilled in the art. Examples of anions of monobasic inorganic or organic acids are: fluoride, bromide, chloride, iodide, nitrate, the anion of an alkanecarboxylic acid having 1-18 carbon atoms and benzoate; examples of anions of dibasic inorganic or organic acids are: sulphate, oxalate, succinate, fumarate, maleate, phthalate and others; examples of tribasic inorganic or organic anions are: phosphate and citrate. Preferred anions X are: fluoride, chloride, bromide, iodide, sulphate, nitrate, phosphate, formate, acetate, propionate, oxalate, butyrate, citrate, succinate, fumarate, maleate, benzoate, phthalate, decanoate, stearate, palmitate and laurate. Particularly preferred anions X are: chloride, bromide, iodide, acetate, laurate, stearate, palmitate, decanoate, nitrate and sulphate. As cation B in the catalyst of the formula above, it is possible to use a cation from the group consisting of alkali or alkaline earth metal cations, quaternary ammonium, phosphonium, arsonium or stibonium cations and ternary sulphonium cations. As alkali or alkaline earth metal cations, mention may here be made of: the lithium, sodium, potassium, rubidium, cesium, magnesium, calcium, strontium and barium cations, preferably the alkali metal cations mentioned, particularly preferably the sodium cation and the potassium cation. According to one embodiment, B has the formula

where Q is N, P, As or Sb and $R_6$, $R_7$, $R_8$, and $R_9$ are each, independently of one another, straight-chain or branched $C_1$-$C_{18}$ alkyl groups or $C_7$-$C_{12}$ aralkyl groups. The anion Y in the transesterification catalyst of the formula above may be a halide ion such as fluoride, chloride, bromide or iodide, preferably bromide or iodide, particularly preferably iodide. However, it can also have the meaning of other anions mentioned under X if in the specific case the anion X is bromide or iodide. The bifunctional transesterification catalyst may be used in an amount of 0.005-5% by weight, or from 0.01-3% by weight, or even further from 0.01-1% by weight, based on the total weight of the transesterification reaction mixture.

In embodiments where transesterification is carried out in reaction columns, insoluble transesterification catalysts which are arranged on intermediate trays or in the middle of packing elements of the reaction column may be used. Examples include: ion-exchange resins having functional groups selected from among tertiary amines, quaternary ammonium groups, with hydroxide, chloride or hydrogen sulphates being mentioned by way of example as counterions, sulphonic acid groups or carboxyl groups, with hydrogen, alkali metals or alkaline earth metals being mentioned by way of example as counterions for both. These functional groups can be bound either directly or via inert chains to the polymer (see for e.g. U.S. Pat. No. 4,062,884, U.S. Pat. No. 4,691,04, and EP 298 167 A). Mention may also be made of alkali metal or alkaline earth metal silicates impregnated on silicon dioxide supports, and also ammonium-exchanged zeolites.

Transesterification can be effected by bringing the reactant dialkyl carbonate, methyl branched primary $C_{16}$-$C_{17}$ alcohol and transesterification catalyst into contact under transesterification reaction conditions and eliminating the reaction by-products as is well known in the art. The reactant dialkyl carbonate and methyl branched primary $C_{16}$-$C_{17}$ alcohol may reacted in molar ratios of 1:10 to 10:1. To produce symmetrical dialkyl carbonates of the formula (I) (i.e. carbonates obtained by transesterification of both ester groups of the reactant dialkyl carbonate), a molar excess of methyl branched primary $C_{16}$-$C_{17}$ alcohol may be used. For example, a molar ratio of reactant alcohol to reactant carbonate of 1:1 to 5:1, or in some embodiments greater than 1:1 to 2:1 may be used. In other embodiments where asymmetrical dialkyl carbonates of the formula (I) (i.e. carbonates obtained by transesterification of only one of the two ester groups of the reactant dialkyl carbonate) are desired, a molar excess of reactant dialkyl carbonate may be used. For example, a molar ratio of reactant alcohol to reactant carbonate of 1:2 to 1:5 may be used.

Transesterification may be carried out at any desired temperature, for example, from about 20° C. to about 290° C. In other embodiments, transesterification is carried out a temperature of from about 75° C. to about 150° C. In still other embodiments, the transesterification is carried out a temperature of from about 100° C. to about 135° C. Furthermore, transesterification may be carried out at, above or below atmospheric pressure. Batch, semi-batch or continuous processes may be used. In some embodiments, transesterification may be carried out in a moisture-free, inert atmosphere under nitrogen, argon or the like. In still other embodiments, a non-reactive organic solvent may be used. Upon completion of transesterification, the dialkyl carbonate of formula (I) may be treated with neutral or acidic filtration aids to neutralize the carbonate product. In some embodiments, the neutral or acidic filtration aids may instead be added directly to the reaction mixture during transesterification. If used, the filtration aids may be separated from the dialkyl carbonate of formula (I) by filtration or centrifugation.

According to one embodiment, the reactant dialkyl carbonate, methyl branched primary $C_{16}$-$C_{17}$ alcohol and transesterification catalyst are brought into contact in a stirred tank reactor and transesterification is carried out at a temperature from about 75° C. to about 150° C. The reaction by-products can be removed continuously during transesterification by distillation. Upon completion of transesterification, traces of unreacted dialkyl carbonate and/or of the alcohol released may be removed by treating the crude product under vacuum at temperatures below 150° C.

According to another embodiment, transesterification is carried out continuously in a reaction column equipped with tower packings and/or internals as described in EP 0033929. The dumped or stacked tower packings to be used are those typically used for distillation. The following are mentioned by way of example: Raschig or Pall rings, Berl-Intalex or Torus saddles, Interpack elements of various materials, such as glass, stoneware, porcelain, carbon, stainless steel, plastics, which may be processed into a mesh-like structure, particularly where metal cloth is used. Dumped and stacked tower packings characterized by a large surface, by thorough wetting and by an adequate residence time of the liquid are preferred. Examples of such packings include Pall and Novolax rings, Berl saddles, BX packings, Montz-Pak, Mellapak, Melladur, Kerapak and CY packings. However, not only packed columns, but also columns with fixed internals may be used for the process according to the present disclosure. Among the columns with fixed internals, those with bubble trays or valve trays having long residence times and a thorough transfer of material are preferred. In general, however, other tray columns, for example columns with sieve trays, bubble trays, valve trays, tunnel trays and centrifugal trays, which in turn may be present in various forms, are also suitable. Other typical representatives of suitable reaction columns are described in EP 0033929.

Reaction columns consisting of two sections, a reaction section with special internals, especially bubble trays, and a pure material transfer section with a stacked transfer packing are particularly preferred.

The column may be operated at temperatures from about 60° C.-250° C. In one embodiment, a solution of the transesterification catalyst in the alcohol intended for the transesterification is fed in directly below the transfer packing. The transesterification catalyst and alcohol solution can be heated beforehand to a temperature from about 100° C.-200° C. The reactant carbonate is fed into the lower part of the column in liquid or gaseous form at a temperature from about 150° C.-250° C. Transesterification takes place in the liquid phase on the column trays and the liquid product carbonate accumulating is discharged at the lower end of the column while the alcohol formed is removed in gaseous form at the head of the column. Pure alcohol formed can be removed at the head of the column whereas the product carbonate accumulates together with the excess reactant alcohol and transesterification catalyst at the bottom of the column. The bottom product may be worked up by methods known from the prior art so that the dialkyl carbonate of formula (I) is obtained in the required purity. The conversion of the reactant carbonate is generally above 99% so that both the distillate and the bottom product are free from reactant carbonate. In another embodiment, the transesterification catalyst is fixedly accommodated in the reaction column and the process is carried out as described above except that there is no addition of transesterification catalyst to the reactant alcohol.

In yet another embodiment, transesterification is performed in a semi-batch process, where the reaction is carried out in a stirred tank reactor surmounted by a column. The column may be of the same type as described for the continuous process. A column consisting of a reaction section, more particularly with bubble trays, and a material transfer section is again preferred. The reactant carbonate is introduced into the stirred tank reactor with part of the reactant alcohol and the transesterification catalyst and is subsequently heated with stirring to a temperature from about 150° C.-250° C. A mixture of reactant carbonate and alcohol evaporates into the reaction column into which reactant alcohol and transesterification catalyst (preheated to a temperature of 80° C.-210° C.) are simultaneously introduced above the reaction zone. The reaction takes place in the same way as in the continuous process. 0 to 100% by weight and preferably 50 to 100% by weight of the quantity of reactant dialkyl carbonate and 0 to 90% by weight and preferably 50 to 80% by weight of the quantity of alcohol used may be initially introduced into the stirred tank reactor, the remaining quantities being introduced into the reaction column in the same way as in the continuous process.

In another variant of the process, only reactant alcohol and transesterification catalyst are initially introduced into the stirred tank reactor, the reactant carbonate being introduced into the stirred tank reactor at the same time as the remaining reactant alcohol is fed into the column.

Because of the unexpected improved physical and chemical properties over state of the art dialkyl carbonates, the dialkyl carbonate of a methyl branched primary $C_{16}$-$C_{17}$ alcohol of formula (I) of the present disclosure may be used in various applications and products, such as in lubrication, cosmetic, and textile applications and products.

Thus, in one embodiment, the dialkyl carbonate of a methyl branched primary $C_{16}$-$C_{17}$ alcohol of formula (I) may be used: in connection with lubricant base fluids, performance fluid components, metal working fluids, low-smoke lubricating compositions for two-phase engines, and in compressor fluids; as a softening agent for textile finishing compositions; in cosmetic compositions for providing good feel and spreadability and compatibility with other oils and pigments; in certain applications and products for unlocking screws, nuts and bolts; and as an expeller to dissolve dirt and grease and remove moisture that may cause power disruption.

In one particular embodiment, there is provided a lubricant composition comprising a lubricating quantity of a dialkyl carbonate of a methyl branched primary $C_{16}$-$C_{17}$ alcohol of formula (I)

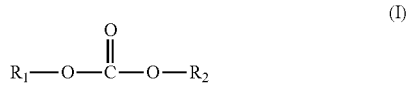

(I)

where $R_1$ is a methyl branched $C_{16}$-$C_{17}$ alkyl group; and $R_2$ has the same meaning as $R_1$ or is an alkyl group having 1 to 20 carbon atoms, an alicyclic group having 3 to 20 carbon atoms or an aralkyl group having 6 to 20 carbon atoms. In a further embodiment, $R_2$ has the same meaning as $R_1$ or is an alkyl group having 1 to 10 carbon atoms, an alicyclic group having 3 to 10 carbon atoms or an aralkyl group having 6 to 10 carbon atoms In some embodiments, a lubricating quantity may range from 0.5% by weight to about 100% by weight, based on the total weight of the lubricant composition. In still other embodiments, a lubricating quantity may range from 1% by weight to about 50% by weight, based on the total weight of the lubricant composition. In still further embodiments, a lubricating quantity may range from 5% by weight to about 30% by weight, based on the total weight of the lubricant composition.

The lubricant composition of the present disclosure is especially useful as an automotive and truck crankcase lubricant; as well as a transmission lubricant, gear lubricant, hydraulic fluid, compressor oil, and diesel or marine lubricant.

In further embodiments, the lubricant composition of the present disclosure further comprises at least one base oil of lubricating viscosity. Base oil as used herein is defined as a base stock or blend of base stocks which is a lubricant component that is produced by a single manufacturer to the same specifications (independent of feed source or manufacturer's location): that meets the same manufacturer's specification; and that is identified by a unique formula, product identification number, or both. Base stocks may be manufactured using a variety of different processes including but not limited to distillation, solvent refining, hydrogen processing, oligomerization, esterification, and rerefining. Rerefined stock shall be substantially free from materials introduced through manufacturing, contamination, or previous use. The base oil may be any natural or synthetic lubricating base oil fraction particularly those having a kinematic viscosity at 100° C. of about 5 centistokes (cSt) to about 20 cSt, preferably about 7 cSt to about 16 cSt, more preferably about 9 cSt to about 15 cSt. Hydrocarbon synthetic oils may include, for example, oils prepared from the polymerization of ethylene, i.e., polyalphaolefin or PAO, or from hydrocarbon synthesis procedures using carbon monoxide and hydrogen gases such as in a Fisher-Tropsch process. A preferred base oil is one that comprises little, if any, heavy fraction; e.g., little, if any, lube oil fraction of viscosity 20 cSt or higher at 100° C.

The base oil may be derived from natural lubricating oils, synthetic lubricating oils or mixtures thereof. Suitable base oil includes base stocks obtained by isomerization of synthetic wax and slack wax, as well as hydrocrackate base stocks produced by hydrocracking (rather than solvent extracting) the aromatic and polar components of the crude. Suitable base oils include those in all API categories I, II, III, IV and V as defined in API Publication 1509, 14th Edition, Addendum I, December 1998. Saturates levels and viscosity indices for Group I, II and III base oils are listed in the table below. Group IV base oils are polyalphaolefins (PAO). Group V base oils include all other base oils not included in Group I, II, III, or IV.

| Group | Saturates (As determined by ASTM D 2007) Sulfur (As determined by ASTM D 2270) | Viscosity Index (As determined by ASTM D 4294, D 4297 or D 3120) |
|---|---|---|
| I | Less than 90% saturates and/or greater than 0.03% sulfur | Greater than or equal to 80 and less than 120 |
| II | Greater than or equal to 90% saturates and less than or equal to 0.03% sulfur | Greater than or equal to 80 and less than 120 |
| III | Greater than or equal to 90% saturates and less than or equal to 0.03% sulfur | Greater than or equal to 120 |

Natural lubricating oils may include animal oils, vegetable oils (for e.g., rapeseed oils, castor oils and lard oil), petroleum oils, mineral oils, and oils derived from coal or shale.

Synthetic oils may include hydrocarbon oils and halo-substituted hydrocarbon oils such as polymerized and inter-polymerized olefins, alkylbenzenes, polyphenyls, alkylated diphenyl ethers, alkylated diphenyl sulfides, as well as their derivatives, analogues and homologues thereof, and the like. Synthetic lubricating oils also include alkylene oxide polymers, interpolymers, copolymers and derivatives thereof wherein the terminal hydroxyl groups have been modified by esterification, etherification, etc. Another suitable class of synthetic lubricating oils comprises the esters of dicarboxylic acids with a variety of alcohols. Esters useful as synthetic oils also include those made from $C_5$-$C_{12}$ monocarboxylic acids and polyols and polyol ethers. Tri-alkyl phosphate ester oils such as those exemplified by tri-n-butyl phosphate and tri-iso-butyl phosphate are also suitable for use as base oils.

Silicon-based oils (such as the polyakyl-, polyaryl-, polyalkoxy-, or polyaryloxy-siloxane oils and silicate oils) comprise another useful class of synthetic lubricating oils. Other synthetic lubricating oils include liquid esters of phosphorus-containing acids, polymeric tetrahydrofurans, polyalphaolefins, and the like.

The base oil may be derived from unrefined, refined, rerefined oils, or mixtures thereof. Unrefined oils are obtained directly from a natural source or synthetic source (for e.g., coal, shale, or tar sand bitumen) without further purification or treatment. Examples of unrefined oils include a shale oil obtained directly from a retorting operation, a petroleum oil obtained directly from distillation, or an ester oil obtained directly from an esterification process, each of which may then be used without further treatment. Refined oils are similar to the unrefined oils except that refined oils have been treated in one or more purification steps to improve one or more properties. Suitable purification techniques include distillation, hydrocracking, hydrotreating, dewaxing, solvent extraction, acid or base extraction, filtration, and percolation, all of which are known to those skilled in the art. Rerefined oils are obtained by treating used oils in processes similar to those used to obtain the refined oils. These rerefined oils are also known as reclaimed or reprocessed oils and often are additionally processed by techniques for removal of spent additives and oil breakdown products.

Base oil derived from the hydroisomerization of wax may also be used, either alone or in combination with the aforesaid natural and/or synthetic base oil. Such wax isomerate oil is produced by the hydroisomerization of natural or synthetic waxes or mixtures thereof over a hydroisomerization catalyst.

The lubricant composition may further include one or more additives such as dispersants, detergents, corrosion/rust inhibitors, antioxidants, anti-wear agents, anti-foamants, friction modifiers, seal swell agents, emulsifiers, VI improvers, pour point depressants, and the like.

The following additives are provided to illustrate those that may be used in the present disclosure, but they are not intended to limit it.

(A) Ashless dispersants: alkenyl succinimides, alkenyl succinimides modified with other organic compounds such as ethylene carbonate, polysuccinimides, and alkenyl succinimides modified with boric acid, alkenyl succinic ester.

(B) Oxidation inhibitors:

1) Phenol type phenolic) oxidation inhibitors: 4,4'-methylenebis (2,6-di-tert-butylphenol), 4,4'-bis(2,6-di-tert-butylphenol), 4,4'-bis(2-methyl-6-tert-butylphenol), 2,2'-(methylenebis(4-methyl-6-test-butyl-phenol), 4,4'-butylidenebis(3-methyl-6-tert-butylphenol), 4,4'-isopropylidenebis(2,6-di-tert-butylphenol), 2,2'-methylenebis(4-methyl-6-nonylphenol), 2,2'-isobutylidene-bis(4,6-dimethylphenol), 2,2'-methylenebis(4-methyl-6-cyclohexylphenol), 2,6-di-tert-butyl4-methylphenol, 2,6-di-tert-butyl4-ethylphenol, 2,4-dimethyl-6-tert-butyl-phenol, 2,6-di-tert-.alpha.-dimethylamino-p-cresol, 2,6-di-tert-4(N,N'dimethylaminomethylphenol), 4,4'-thiobis(2-methyl-6-tert-1-butylphenol), 2,2'-thiobis(4-methyl-6-tert-butylphenol), bis(3-methyl-4-hydroxy-5-tert-butylbenzyl)-sulfide, and bis (3,5-di-tert-butyl4-hydroxybenzyl).

2) Diphenylamine type oxidation inhibitor: alkylated diphenylamine, phenyl-.alpha.-naphthylamine, and alkylated .alpha.-naphthylamine.

3) Other types: metal dithiocarbamate (e.g., zinc dithiocarbamate), and methylenebis (dibutyldithiocarbamate).

(C) Rust inhibitors (Anti-rust agents):

1) Nonionic polyoxyethylene surface active agents: polyoxyethylene lauryl ether, polyoxyethylene higher alcohol ether, polyoxyethylene nonylphenyl ether, polyoxyethylene octylphenyl ether, polyoxyethylene octyl stearyl ether, polyoxyethylene oleyl ether, polyoxyethylene sorbitol monostearate, polyoxyethylene sorbitol mono-oleate, and polyethylene glycol monooleate.

2) Other compounds: stearic acid and other fatty acids, dicarboxylic acids, metal soaps, fatty acid amine salts, metal salts of heavy sulfonic acid, partial carboxylic acid ester of polyhydric alcohol, and phosphoric ester.

(D) Demulsifiers: addition product of alkylphenol and ethyleneoxide, polyoxyethylene alkyl ether, and polyoxyethylene sorbitane ester.

(E) Extreme pressure agents (EP agents): sulfurized oils, diphenyl sulfide, methyl trichlorostearate, chlorinated naphthalene, benzyl iodide, fluoroalkylpolysiloxane, and lead naphthenate.

(F) Friction modifiers: fatty alcohol, fatty acid, amine, borated ester, and other esters.

(G) Multifunctional additives: sulfurized oxymolybdenum dithiocarbamate, sulfurized oxymolybdenum organo phosphorodithioate, oxymolybdenum monoglyceride, oxymolybdenum diethylate amide, amine-molybdenum complex compound, and sulfur-containing molybdenum complex compound.

(H) Viscosity Index improvers: polymethacrylate type polymers, ethylene-propylene copolymers, styrene-isoprene copolymers, hydrated styrene-isoprene copolymers, polyisobutylene, and dispersant type viscosity index improvers.

(I) Pour point depressants: polymethyl methacrylate.

(K) Foam Inhibitors: alkyl methacrylate polymers and dimethyl silicone polymers.

(L) Wear inhibitors: zinc dialkyldithiophosphate (Zn-DTP, primary alkyl type & secondary alkyl type).

In another embodiment, there is provided a packaged product comprising: a) a container having at least an outlet; and b) a dialkyl carbonate of the formula (I) of the present disclosure within the container.

According to one embodiment, the packaged product of the present disclosure comprises a container having a closure means, such as a lid, cover, cap, or plug to seal the container. In another embodiment, the sealed container also has a nozzle or pour spout. The sealed container may have the shape of a cylinder, oval, round, rectangle, canister, tub, square or jug and contains the catalyst mixture. In some embodiments, the sealed container is padded with an inert gas, such as nitrogen.

The container may be made from any material, such as steel, glass, aluminium, cardboard, tin-plate, plastics including HDPE, PP, PVC, PET, OPP, PE or polyamide and including mixtures, laminates or other combinations of these. The dialkyl carbonate of formula (I) of the present disclosure may be dispensed from the container through the outlet. In one embodiment, the dialkyl carbonate of formula (I) of the present disclosure is dispensed from a nozzle when the nozzle is activated. In another embodiment, the dialkyl carbonate of formula (I) of the present disclosure is dispensed via a pour spout.

EXAMPLES

Example 1. Synthesis of Dialkyl Carbonate of the Present Disclosure from Neodol® 67

The Neodol® 67 alcohol and dimethyl carbonate (DMC) were mixed at 2:1 molar ratio. The transesterification reaction was done in a stirred tank batch reactor with a base catalyst. The DMC/methanol mixture was removed during transesterification. After transesterification was complete, the lights including DMC and methanol were removed by vacuum at an elevated temperature. The dialkyl carbonate product, residual Neodol® 67 alcohol and the mono methyl carbonate were separated by heat and vacuum.

Properties of the dialkyl carbonate from Neodol® 67 alcohol and a dialkyl carbonate based on a branched Oxo $C_{14}$-$C_{15}$ alcohol are compared below:

|  | Dialkyl carbonate from Neodol ® 67 alcohol | Dialkyl carbonate from branched Oxo $C_{14}$-$C_{15}$ alcohol |
|---|---|---|
| Kinematic viscosity (cSt, 100° C.) | 5.8862 | 4.1 |
| Kinematic viscosity (cSt, 40° C.) | 28.027 | 18 |
| Viscosity index | 148.5 | 126 |
| Pour point (° C.) | −32 | −36 |

Note:
1 The pour point of the dialkyl carbonate from Neodol ® 67alcohol was based on ASTM D97.

2. Data for the dialkyl carbonate based on branched Oxo C14-15 alcohol was from "Synthetics, Mineral Oils, and Bio-Based Lubricants: Chemistry and Technology, Second Edition, by Leslie R. Rudnick, Page 251).

Consideration must be given to the fact that although this disclosure has been described and disclosed in relation to certain preferred embodiments, obvious equivalent modifications and alterations thereof will become apparent to one of ordinary skill in this art upon reading and understanding this specification and the claims appended hereto. The present disclosure includes the subject matter defined by any combination of any one of the various claims appended hereto with any one or more of the remaining claims, including the incorporation of the features and/or limitations of any dependent claim, singly or in combination with features and/or limitations of any one or more of the other dependent claims, with features and/or limitations of any one or more of the independent claims, with the remaining dependent claims in their original text being read and applied to any independent claim so modified. This also includes combination of the features and/or limitations of one or more of the independent claims with the features and/or limitations of another independent claim to arrive at a modified independent claim, with the remaining dependent claims in their original text being read and applied to any independent claim so modified. Accordingly, the presently disclosed invention is intended to cover all such modifications and alterations, and is limited only by the scope of the claims which follow, in view of the foregoing and other contents of this specification.

What is claimed is:

1. A dialkyl carbonate of a methyl branched primary $C_{16}$-$C_{17}$ alcohol having a structure according to formula (I):

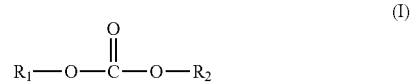

where $R_1$ is a methyl branched $C_{16}$-$C_{17}$ alkyl group; and $R_2$ has the same meaning as $R_1$ or is an alkyl group having 1 to 20 carbon atoms, an alicyclic group having 3 to 20 carbon atoms or an aralkyl group having 6 to 20 carbon atoms.

2. The dialkyl carbonate of claim 1 wherein $R_2$ is a methyl branched $C_{16}$-$C_{17}$ alkyl group.

3. The dialkyl carbonate of claim 1 wherein $R_2$ is an alkyl group having 1 to 10 carbon atoms.

4. The dialkyl carbonate of claim 1 wherein $R_2$ is an alkyl group having 1 to 4 carbon atoms.

5. The dialkyl carbonate of claim 1 wherein $R_2$ is a methyl or ethyl group.

6. The dialkyl carbonate of claim 1 wherein $R_2$ is an aralkyl group having 6 to 10 carbon atoms.

7. A process for preparing a dialkyl carbonate of a methyl branched primary $C_{16}$-$C_{17}$ alcohol having a structure according to formula (I):

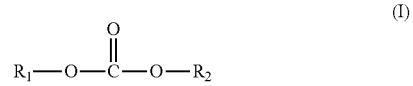

where $R_1$ is a methyl branched $C_{16}$-$C_{17}$ alkyl group; and $R_2$ has the same meaning as $R_1$ or is an alkyl group having 1 to 20 carbon atoms, an alicyclic group having 3 to 20 carbon atoms or an aralkyl group having 6 to 20 carbon atoms comprising transesterifying a reactant dialkyl carbonate having a structure according to formula (II):

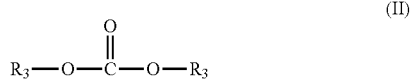

where $R_3$ is an alkyl group having 1 to 20 carbon atoms, an alicyclic group having 3 to 20 carbon atoms or an aralkyl group having 6 to 20 carbon atoms with a methyl branched primary $C_{16}$-$C_{17}$ alcohol and optionally a transesterification catalyst.

8. The process according to claim 7 wherein $R_3$ is a lower alkyl group having 1 to 4 carbon atoms.

9. The process according to claim 8 wherein $R_3$ is methyl.

10. The process according to claim 7 wherein the methyl branched primary $C_{16}$-$C_{17}$ alcohol is a monomethyl branched primary $C_{16}$-$C_{17}$ alcohol having the following structure:

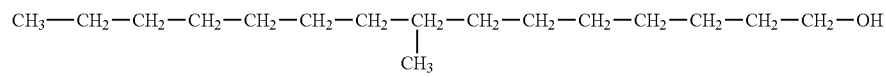

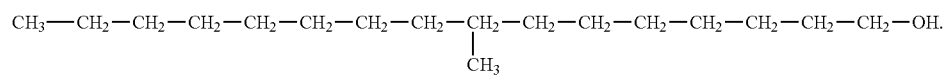

11. A dialkyl carbonate of a methyl branched primary $C_{16}$-$C_{17}$ alcohol having a structure according to formula (I):

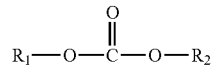
(I)

where $R_1$ is a methyl branched $C_{16}$-$C_{17}$ alkyl group; and
$R_2$ has the same meaning as $R_1$ or is an alkyl group having 1 to 20 carbon atoms, an alicyclic group having 3 to 20 carbon atoms or an aralkyl group having 6 to 20 carbon atoms prepared by the process of claim 7.

12. A lubricant composition comprising a lubricating quantity of a dialkyl carbonate of a methyl branched primary $C_{16}$-$C_{17}$ alcohol having a structure according to formula (I)

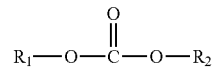
(I)

where $R_1$ is a methyl branched $C_{16}$-$C_{17}$ alkyl group; and
$R_2$ has the same meaning as $R_1$ or is an alkyl group having 1 to 20 carbon atoms, an alicyclic group having 3 to 20 carbon atoms or an aralkyl group having 6 to 20 carbon atoms.

13. The lubricant composition of claim 12 further comprising at least one base oil.

14. The lubricant composition of claim 13 further comprising one or more additives comprising a dispersant, a detergent, a corrosion/rust inhibitor, an antioxidant, an anti-wear agent, an anti-foamant, a friction modifier, a seal swell agent, an emulsifiers, a VI improver or a pour point depressant.

* * * * *